(12) United States Patent
Enjoji et al.

(10) Patent No.: US 10,876,974 B2
(45) Date of Patent: Dec. 29, 2020

(54) INSPECTION DEVICE, INSPECTION SYSTEM, AND INSPECTION METHOD

(71) Applicant: AFI Corporation, Kyoto (JP)

(72) Inventors: Takaharu Enjoji, Tokyo (JP); Yoshikazu Wakizaka, Takarazuka (JP); Satoshi Uchida, Hachiouji (JP); Eiko Kato, Tama (JP); Masayo Takano, Kobe (JP)

(73) Assignee: AFI CORPORATION, Kyoto (JP)

( * ) Notice: Subject to any disclaimer, the term of this patent is extended or adjusted under 35 U.S.C. 154(b) by 0 days.

(21) Appl. No.: 16/668,550

(22) Filed: Oct. 30, 2019

(65) Prior Publication Data

US 2020/0064274 A1 Feb. 27, 2020

Related U.S. Application Data

(62) Division of application No. 15/578,193, filed as application No. PCT/JP2016/079676 on Oct. 5, 2016, now Pat. No. 10,495,580.

(30) Foreign Application Priority Data

Oct. 7, 2015 (JP) ................................. 2015-199470

(51) Int. Cl.
*G01N 21/00* (2006.01)
*G01N 21/88* (2006.01)
(Continued)

(52) U.S. Cl.
CPC ........... *G01N 21/8851* (2013.01); *C12M 1/34* (2013.01); *C12Q 1/04* (2013.01); *C12Q 1/06* (2013.01);
(Continued)

(58) Field of Classification Search
CPC ........ G01N 21/29; G01N 33/32; G01N 21/05; G01N 21/293; G01N 33/2888
(Continued)

(56) References Cited

U.S. PATENT DOCUMENTS

| 8,775,053 B2 | 7/2014 | Nishijima et al. |
| 2003/0159932 A1 | 8/2003 | Betts et al. |

(Continued)

FOREIGN PATENT DOCUMENTS

| EP | 1202812 B1 | 5/2007 |
| JP | 2003-504196 A | 2/2003 |

(Continued)

OTHER PUBLICATIONS

International Patent Application No. PCT/JP2016/079676; Int'l Preliminary Report on Patentability; dated Apr. 19, 2018; 7 pages.
(Continued)

*Primary Examiner* — Md M Rahman
(74) *Attorney, Agent, or Firm* — BakerHostetler

(57) ABSTRACT

An inspection device (1) inspects an amount of dielectric particles contained in a sample liquid. The inspection device includes a dielectric collection unit (3), a pump unit (10) and an AC voltage supply unit (11). The dielectric collection unit includes at least one pair of electrodes (41, 42) and a flow channel (13) extending in a predetermined direction on the pair of electrodes. The pump unit is configured to feed the sample liquid to follow the flow channel in the predetermined direction. The AC voltage supply unit is configured to supply, to the pair of electrodes, an AC voltage with a predetermined frequency to cause dielectrophoresis for dielectric particles in the fed sample liquid. The dielectric collection unit includes a plurality of slit regions (Rs) aligned in the predetermined direction between the pair of electrodes. Each of the plurality of slit regions is separated from each other within the flow channel.

7 Claims, 14 Drawing Sheets

(51) Int. Cl.
*G01N 15/06* (2006.01)
*G01N 27/26* (2006.01)
*C12Q 1/06* (2006.01)
*C12M 1/34* (2006.01)
*C12Q 1/04* (2006.01)
*G01N 15/00* (2006.01)
*G01N 21/64* (2006.01)

(52) U.S. Cl.
CPC ......... *G01N 15/00* (2013.01); *G01N 15/0612* (2013.01); *G01N 15/0656* (2013.01); *G01N 21/64* (2013.01); *G01N 21/8806* (2013.01); *G01N 27/26* (2013.01); *G01N 2015/0053* (2013.01); *G01N 2015/0065* (2013.01)

(58) Field of Classification Search
USPC ........................................................ 356/441
See application file for complete search history.

(56) References Cited

U.S. PATENT DOCUMENTS

| 2005/0157393 A1 | 7/2005 | Hasegawa et al. |
| 2011/0170105 A1 | 7/2011 | Cui et al. |
| 2013/0144503 A1 | 6/2013 | Nishijima et al. |
| 2014/0061049 A1 | 3/2014 | Lo et al. |

FOREIGN PATENT DOCUMENTS

| JP | 2008-196860 A | | 8/2008 |
| JP | 2012-071256 A | | 4/2012 |
| WO | WO2001052996 A1 | * | 1/2001 |
| WO | WO 2007/046484 A1 | | 4/2007 |
| WO | WO 2007/046485 A1 | | 4/2007 |
| WO | WO 2009/140796 A1 | | 11/2009 |
| WO | WO 2012/023182 A1 | | 2/2012 |
| WO | WO 2013/018497 A1 | | 2/2013 |

OTHER PUBLICATIONS

Form PCT/ISA/210 issued in connection with International Patent Application No. PCT/JP2016/079676 dated Nov. 22, 2016.
"Dielectrophoretic separation and manipulation of live and heat-treated cells of Listeria on microfabricated devices with interdigitated electrodes" Apr. 24, 2002, Li, H. et al.
European Patent Application No. 16853650.6; Extended Search Report; dated Apr. 24, 2019; 11 pages.
Japan Patent Application No. 2017-030387; Notice of Reasons for Refusal; dated Oct. 6, 2020; 8 pages.

* cited by examiner

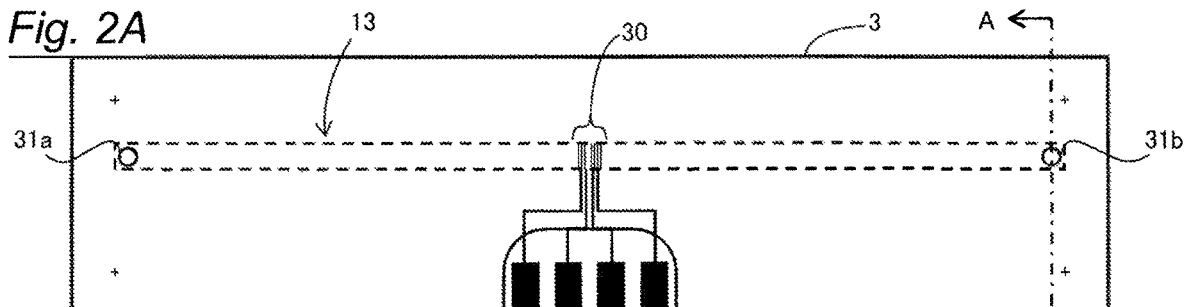
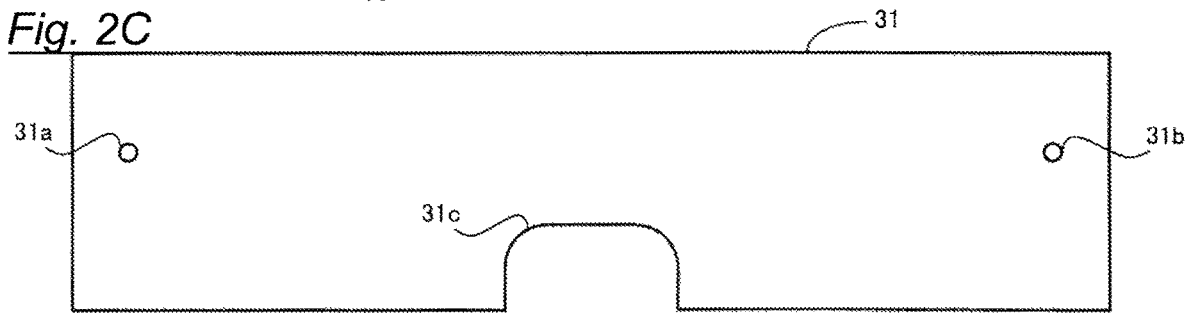
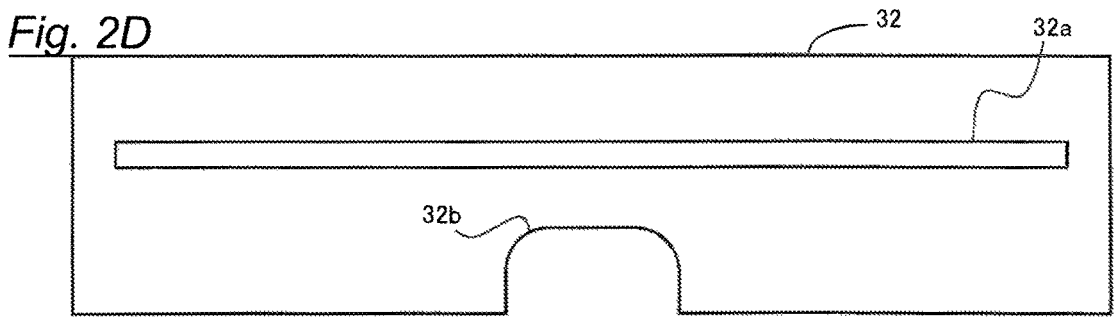
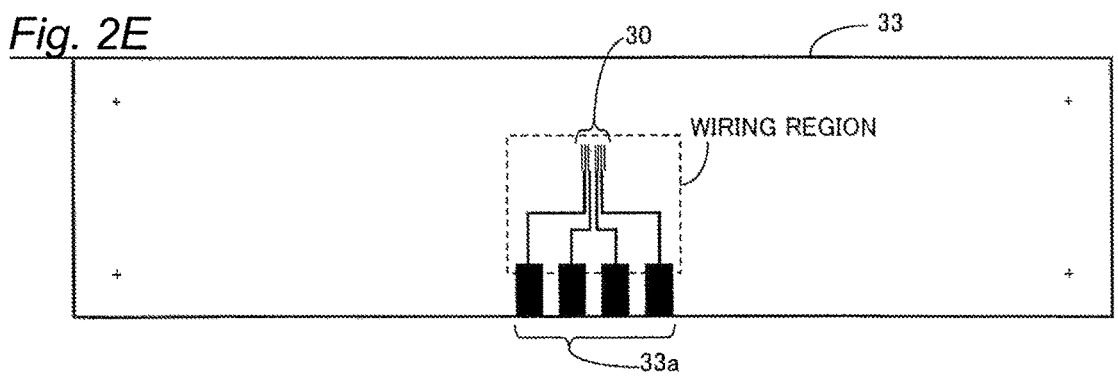

42 Rs 41

42 Rs 41

0 CFU $0.7 \times 10^6$ CFU $1.4 \times 10^6$ CFU $2.8 \times 10^6$ CFU $4.2 \times 10^6$ CFU

INSPECTION DEVICE, INSPECTION SYSTEM, AND INSPECTION METHOD

CROSS REFERENCE TO RELATED APPLICATIONS

This application a divisional of U.S. patent application Ser. No. 15/578,193, filed Nov. 29, 2017, which is the National Stage of International Application No. PCT/JP2016/079676, filed Oct. 5, 2016, which claims the benefit of Japanese application number 2015-199470, filed Oct. 7, 2015 the contents of each of which are incorporated herein by reference in their entirety.

TECHNICAL FIELD

The present invention relates to an inspection device, an inspection system, and an inspection method for inspecting dielectric particles such as bacteria and cells in a sample liquid.

BACKGROUND ART

An inspection method by using dielectrophoresis is known as inspecting dielectric particles such as bacteria and cells contained in a sample liquid.

For example, Patent Literature 1 discloses a microorganism detection method for the purpose of efficiently counting a number of minute particles such as bacteria and microorganisms contained in a sample solution by using dielectrophoresis. In the method in Patent Literature 1, a detection region on a detection substrate, on which a pair of thin film electrodes are formed, is segmented into detection segments that divide the entire length of each linear portion of the electrode gap into several tens of pieces. On each of the detection segments, the number of minute particles each of which having one end trapped to an edge of the electrodes by dielectrophoresis is counted in the method in Patent Literature 1. Then, sequentially scanning the detection segments to sum the number of minute particles is done, whereby the total number of minute particles that exist in the detection region is detected.

CITATION LIST

Patent Literature

Patent Literature 1: Japanese Unexamined Patent Application Publication No. 2008-196860

SUMMARY OF INVENTION

Technical Problem

In the microorganism detection method in Patent Literature 1, dielectrophoresis is applied to trap one end of a minute particle to an edge of the electrodes on each detection segment, and then the immobilized minute particles are counted one by one. Therefore, it takes time and effort to detect the total number of minute particles, and the effort is wasted.

An object of the present invention is to provide an inspection device, an inspection system, and an inspection method capable of easily inspecting the amount of bacteria, cells, and the like contained in a sample liquid.

Solution to Problem

The inspection device according to one aspect of the present invention is a device for inspecting an amount of dielectric particles contained in a sample liquid. The inspection device includes a dielectric collection unit, a pump unit and an AC voltage supply unit. The dielectric collection unit includes at least one pair of electrodes and a flow channel extending in a predetermined direction on the pair of electrodes. The pump unit is configured to feed the sample liquid to follow the flow channel in the predetermined direction. The AC voltage supply unit is configured to supply, to the pair of electrodes, an AC voltage with a predetermined frequency to cause dielectrophoresis for dielectric particles in the fed sample liquid. The dielectric collection unit includes a plurality of slit regions aligned in the predetermined direction between the pair of electrodes. Each of the plurality of slit regions is separated from each other within the flow channel.

The inspection system according to one aspect of the present invention includes the inspection device and a display unit. The inspection device further includes an imaging unit for capturing the image of a predetermined region in which the plurality of slit regions are aligned. The display unit displays the image captured by the imaging unit of the inspection device.

The inspection method according to one aspect of the present invention is a method for inspecting an amount of dielectric particles contained in a sample liquid. The method includes feeding the sample liquid to follow a flow channel in a predetermined direction in a dielectric collection unit, the dielectric collection unit including at least one pair of electrodes and the flow channel extending in the predetermined direction on the pair of electrodes. The method includes supplying, to the pair of electrodes, an AC voltage with a predetermined frequency to cause dielectrophoresis for dielectric particles in the fed sample liquid. The method includes counting slits saturated with the dielectric particles among a plurality of slits aligned in the predetermined direction between the pair of electrodes in the dielectric collection unit.

According to the inspection device, the inspection system, and the inspection method according to the present invention, counting the slits saturated with dielectric particles such as bacteria and cells allows the amount of bacteria, cells, and the like contained in the sample liquid to be easily inspected.

BRIEF DESCRIPTION OF DRAWINGS

FIGS. 2A to 2E are diagrams for explaining the collection unit in the dielectrophoresis device of the present system.

EMBODIMENT OF THE INVENTION

Figure 1:
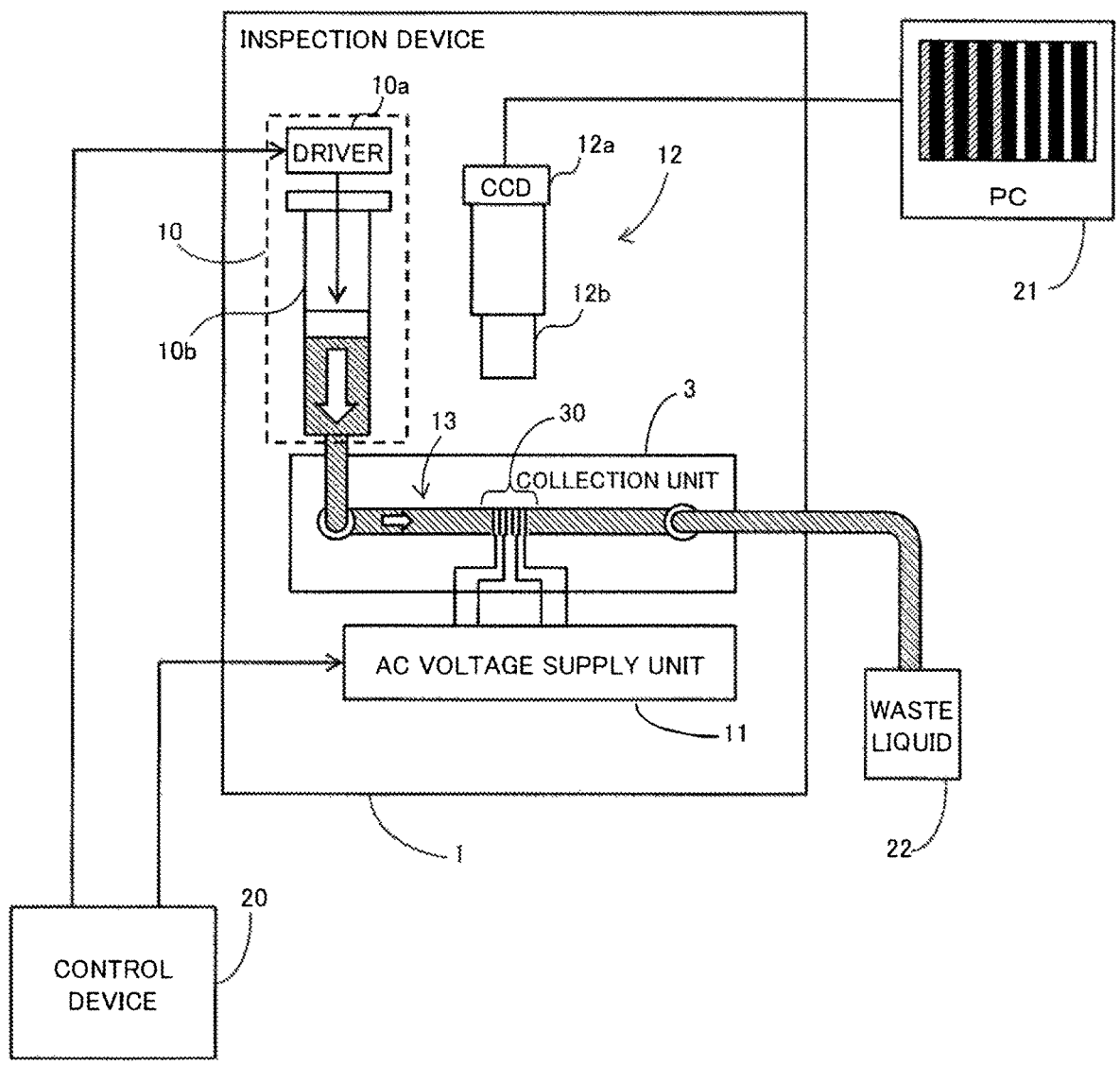
FIG. 1 is a block diagram showing a configuration of the inspection system according to a first embodiment.

In the following, embodiments of an inspection device, an inspection system, and an inspection method using dielectrophoresis according to the present invention will be described with reference to the accompanying drawings. It should be noted that in each of the following embodiments, the same reference numerals are given to the same constituent elements.

First Embodiment

1. Configuration 1-1. System Configuration

The overall configuration of the inspection system according to a first embodiment will be described with reference to FIG. 1. FIG. 1 is a block diagram showing a configuration of the inspection system according to the first embodiment. The inspection system according to the present embodiment includes a dielectrophoresis device 1, a control device 20, an information processing device 21, and a waste liquid chamber 22. The present inspection system is a system for performing inspection of bacteria and the like by using dielectrophoresis of bacteria and cells in a sample liquid (sample) in the dielectrophoresis device 1. In the present system, the dielectrophoresis device 1 is controlled by the control device 20, and the state in which inspection objects such as bacteria are collected in the dielectrophoresis device 1 is displayed in the information processing device 21.

The dielectrophoresis device 1 includes a pump unit 10, an AC (alternating-current) voltage supply unit 11, an imaging unit 12, and a collection unit 3. The dielectrophoresis device 1 is an example of an inspection device in the present embodiment.

The pump unit 10 is constituted by, for example, a syringe pump, and includes a driver 10a and a sample syringe 10b. The driver 10a is configured to include a motor or the like, and drive control is performed by the control device 20. The sample syringe 10b is a syringe for holding a sample liquid. The collection unit 3 is connected to the liquid feeding part of the sample syringe 10b. In the pump unit 10, the velocity of flow and the amount of flow are appropriately set by the drive control of the driver 10a, whereby the sample liquid is fed from the sample syringe 10b to the collection unit 3.

The collection unit 3 includes a flow channel 13 through which the sample liquid flows in a predetermined direction (liquid flow direction) and a microelectrode unit 30 provided in the flow channel 13. The sample liquid fed from the pump unit 10 flows through the flow channel 13 in the collection unit 3 to be drained into the waste liquid chamber 22. The microelectrode unit 30 includes an electrode group formed on the order of micron. In the collection unit 3, when the sample liquid flows on the microelectrode unit 30 in the flow channel 13, a predetermined AC voltage is supplied from the AC voltage supply unit 11 to the microelectrode unit 30. Thus, the bacteria and the like of the inspection objects in the sample liquid cause dielectrophoresis to be collected by the microelectrode unit 30. The collection unit 3 is an example of a dielectric collection unit for collecting dielectric particles such as bacteria in the microelectrode unit 30. Details of the configuration of the collection unit 3 will be described below.

The AC voltage supply unit 11 includes, for example, a function generator. The AC voltage supply unit 11 generates an AC voltage having a desired frequency and voltage amplitude under the control of the control device 20 to supply the AC voltage to the microelectrode unit 30 of the collection unit 3.

The imaging unit 12 includes an image pickup element 12a such as a CCD image sensor or a CMOS image sensor, and an optical microscope module 12b. The optical microscope module 12b may be a phase contrast microscope or an epi illumination microscope. The optical microscope module 12b may be configured to be switchable between a phase contrast microscope and an epi illumination microscope with lens exchange or the like. In addition, when fluorescence observation is performed, a fluorescence filter can be appropriately used. The imaging unit 12 captures an image of a predetermined region in the microelectrode unit 30 in the collection unit 3 (details will be described below) and outputs the captured image to the information processing device 21. The imaging operation of the imaging unit 12 may be controlled by the control device 20 or may be controlled by the information processing device 21.

The control device 20 includes, for example, a CPU and an MPU. The control device 20 controls the operation of the dielectrophoresis device 1 such as liquid feeding of the sample liquid by the pump unit 10 and supply of the AC voltage by the AC voltage supply unit 11. The control device 20 includes an internal memory such as a flash memory, and implements various kinds of functions by performing arithmetic processing using various data or the like based on a program stored in the internal memory. The control device 20 may include a hardware circuit such as an electronic circuit designed for exclusive use or a reconfigurable electronic circuit (ASIC, FPGA, or the like). The function of the control device 20 may be implemented by cooperation of hardware and software, or may be implemented only by hardware (electronic circuit).

The information processing device 21 includes, for example, a personal computer. The information processing device 21 includes a liquid crystal display or an organic electroluminescent display (display unit), and displays a captured image of the imaging unit 12. The information processing device 21 includes an internal memory such as a flash memory and implements various kinds of functions based on a program stored in the internal memory. For example, the information processing device 21 performs image analysis of the captured image of the imaging unit 12 and counts the number of regions (slits) meeting predetermined conditions in the captured image. The information processing device 21 may control the imaging operation of the imaging unit 12. In addition, the information processing device 21 and the control device 20 may be integrally configured by implementing various kinds of functions of the control device 20 in the information processing device 21. The information processing device 21 is an example of a display unit in the present embodiment and is an example of an image analysis unit for analyzing the imaging result of the imaging unit 12.

The waste liquid chamber 22 is a chamber for storing the sample liquid flowing through the collection unit 3 of the dielectrophoresis device 1. The waste liquid chamber 22 may be incorporated inside the dielectrophoresis device 1.

1-2. Configuration of Collection Unit

The configuration of the collection unit 3 will be described below with reference to FIGS. 2A to 4.

FIG. 2A shows a plan view of the collection unit 3. FIG. 2B is a cross-sectional view taken along the line A-A' of the collection unit 3 shown in FIG. 2A. The collection unit 3 has an approximately rectangular flat plate shape as shown in FIG. 2A. In addition, as shown in FIG. 2B, the collection unit 3 includes a cover plate 31, a spacer 32, and an electrode film 33, and has a structure in which these are sequentially superimposed in the thickness direction.

FIG. 2C shows a plan view of the cover plate 31 in the collection unit 3. FIG. 2D shows a plan view of the spacer tape 32. FIG. 2E shows a plan view of the electrode film 33.

The cover plate 31 is a plate member formed of, for example, a transparent acrylic plate or the like. As shown in FIG. 2C, the cover plate 31 is provided with two insertion holes 31a and 31b and a cut-away part 31c. The insertion holes 31a and 31b respectively correspond to the start point and the end point of the flow channel 13 in the collection unit 3 (see FIG. 2A). The cut-away part 31c is famed in a position corresponding to an electrode pad 33a on the electrode film 33 in the cover plate 31.

The spacer 32 is a member formed of, for example, a transparent PET (polyester) tape. In the spacer 32, a rectangular hole 32a corresponding to the flow channel 13 and a cut-away part 32b having the same shape as the cut-away part 31c of the cover plate 31 are formed. The spacer 32 adheres to the cover plate 31 and the electrode film 33 on the respective principal surfaces with an adhesive such as 3M (registered trademark) 9969, and the space between the cover plate 31 and the electrode film 33 (that is, the height of the flow channel 13) is fixed to a predetermined width (for example, 0.1 mm).

The electrode film 33 is a member provided with the microelectrode unit 30 on a transparent film base material such as a PEN (polyethylene naphthalate) film. The microelectrode unit 30 is electrically connected to the electrode pad 33a in the wiring region (details will be described below) on the principal surface of the electrode film 33. The microelectrode unit 30 and the electrode pad 33a are formed of a metallic material such as chromium, for example, by vapor deposition or sputtering.

The collection unit 3 is electrically connected to the AC voltage supply unit 11 at the electrode pad 33a (see FIG. 1). As shown in FIG. 2A, the electrode pad 33a is exposed by the cut-away parts 31c and 32b in a state where the cover plate 31, the spacer 32, and the electrode film 33 are superimposed on each other. Therefore, the collection unit 3 can easily be electrically connected to the AC voltage supply unit 11.

The flow channel 13 of the collection unit 3 is formed by the spacer 32, which closely sticks the cover plate 31 to the electrode film 33 with a predetermined space apart around the rectangular hole 32a. By removably connecting the sample syringe 10b and the waste liquid chamber 22 respectively to the two insertion holes 31a and 31b positioned at both ends of the flow channel 13, causing the sample liquid to flow through the flow channel 13 can be easily achieved. As described above, electrical connection and flow channel connection in the collection unit 3 can be easily performed. Thus, the collection unit 3 can be easily thrown away or reused after collecting bacteria and the like in the dielectrophoresis device 1.

Figure 3:
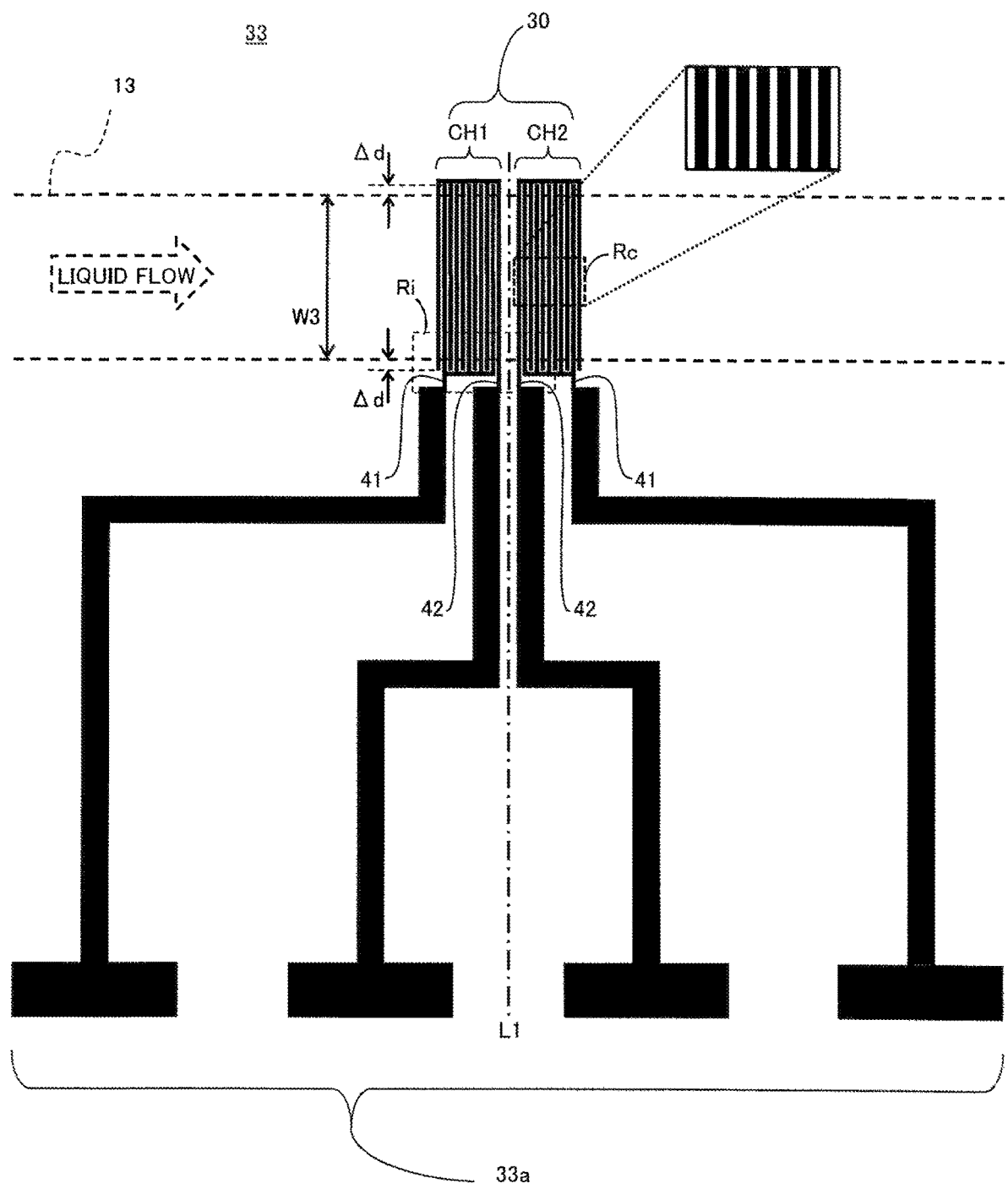
FIG. 3 is an enlarged view of the wiring region of the film electrodes in the collection unit.

FIG. 3 is an enlarged view of the wiring region in the electrode film 33 in FIG. 2E. In the present embodiment, the microelectrode unit 30 in the electrode film 33 includes two sets of electrode pairs CH1 and CH2. The AC voltage from the AC voltage supply unit 11 is supplied to each of the electrodes of the first and second electrode pairs CH1 and CH2 through the electrode pad 33a. The first and second electrode pairs CH1 and CH2 are formed line-symmetrically with respect to the center line L1. In the following, the explanation of the first electrode pair CH1 will be exemplified.

The first electrode pair CH1 includes two electrodes 41 and 42. Each of the electrodes 41 and 42 has a pectinate shape arranged at equal intervals. A plurality of protruding parts in the pectinate shape of the two electrodes 41 and 42 are alternately arranged at predetermined intervals in the liquid flow direction of the flow channel 13. Each protruding part of the electrodes 41 and 42 extends in a direction intersecting (orthogonal to) the liquid flow direction. The same arrangement also applies to electrodes 41 and 42 of the second electrode pair CH2.

Figure 4:
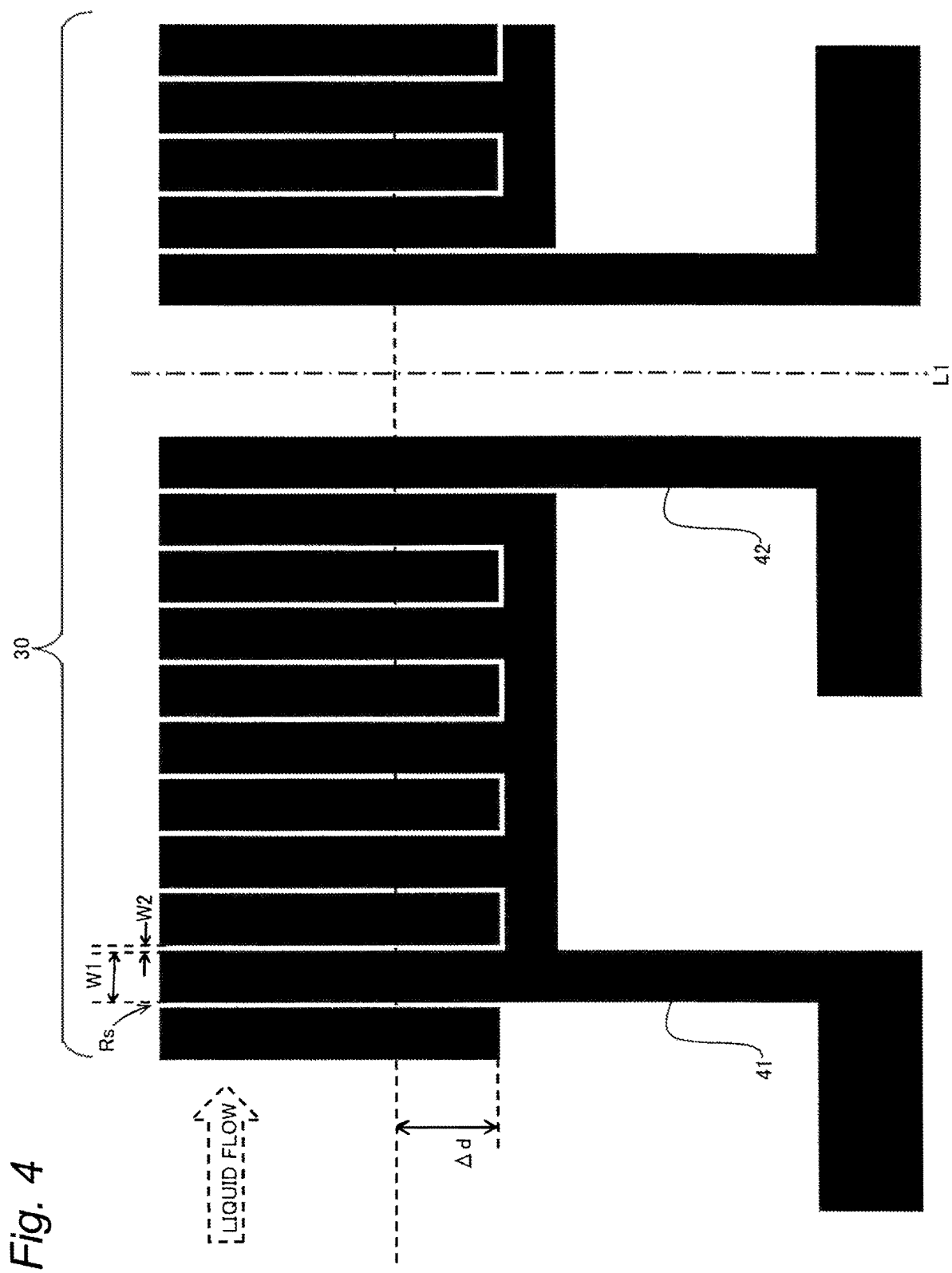
FIG. 4 is an enlarged view of the microelectrode unit in the wiring region.

FIG. 4 is an enlarged view of the microelectrode unit 30 in a region Ri near the edge of the flow channel 13. In the microelectrode unit 30, slit shaped regions Rs each having a predetermined width W2 (hereinafter referred to as "slit region") are formed by a slit between each protruding part of the electrodes 41 and 42 on the flow channel 13. As shown in FIG. 4, a plurality of slit regions Rs align in the liquid flow direction between the pair of electrodes 41 and 42. The width W2 of each slit region Rs is set to a predetermined value, for example, from 10 .mu.m to 20 .mu.m. On the other hand, the width W1 of a protruding part of the electrodes 41 and 42 is, for example, 100 .mu.m. The width W2 of the slit region Rs may be set within the range of 1 .mu.m to 50 .mu.m.

In the present embodiment, the microelectrode unit 30 and the flow channel 13 are set in such a manner that each protruding part of the electrodes 41 and 42 is forced out the flow channel 13 by a predetermined length .DELTA.d. In other words, the region connecting the plurality of slit regions Rs between the pair of electrodes 41 and 42 on the electrode film 33 is arranged outside the flow channel 13. Thus, the plurality of slit regions Rs, which are aligned in the predetermined direction in which the flow channel 13 extends (liquid flow direction), are separated from each other without being connected in the flow channel 13. For example, the length .DELTA.d by which both ends of the electrodes 41 and 42 is out of the flow channel 13 is set to 0.3 mm as compared with the width W3 of the flow channel 13 (see FIG. 3) being set to 3 mm. In addition, the protruding part thickness of each of the electrodes 41 and 42 is, for example, about 100 nm.

In the present inspection system, when the dielectrophoresis of bacteria and the like is performed in the dielectrophoresis device 1, as shown in FIG. 3, a region Rc in which the protruding parts of the electrodes 41 and 42 are sequentially aligned from the upstream side of the flow channel 13 in the microelectrode unit 30 is captured by the imaging unit 12. Thus, a captured image in which it is easy to measure the number of displayed slit regions Rs, that is, to count the slits (Rs) can be obtained.

If the slit regions Rs are connected to each other in the flow channel 13, it is considered to cause, for example, a situation such that bacteria and the like collected in the slit regions Rs on the upstream side move to the slit regions Rs on the downstream side while the dielectrophoresis force between the electrodes 41 and 42 is maintained. On the contrary, separating each slit region Rs in the flow channel 13 as described above allows the collected bacteria and the like between the plurality of slit regions Rs to be prevented from moving, and inspection of the amount of bacteria by counting the slits (Rs) to be easily performed (hereinafter, "slit region Rs" may be abbreviated as "slit Rs").

2. Operation and Inspection Method

The operation of the present system and the inspection method in the present system will be described below.

2-1. Principle of Inspection Method

Figure 5A:
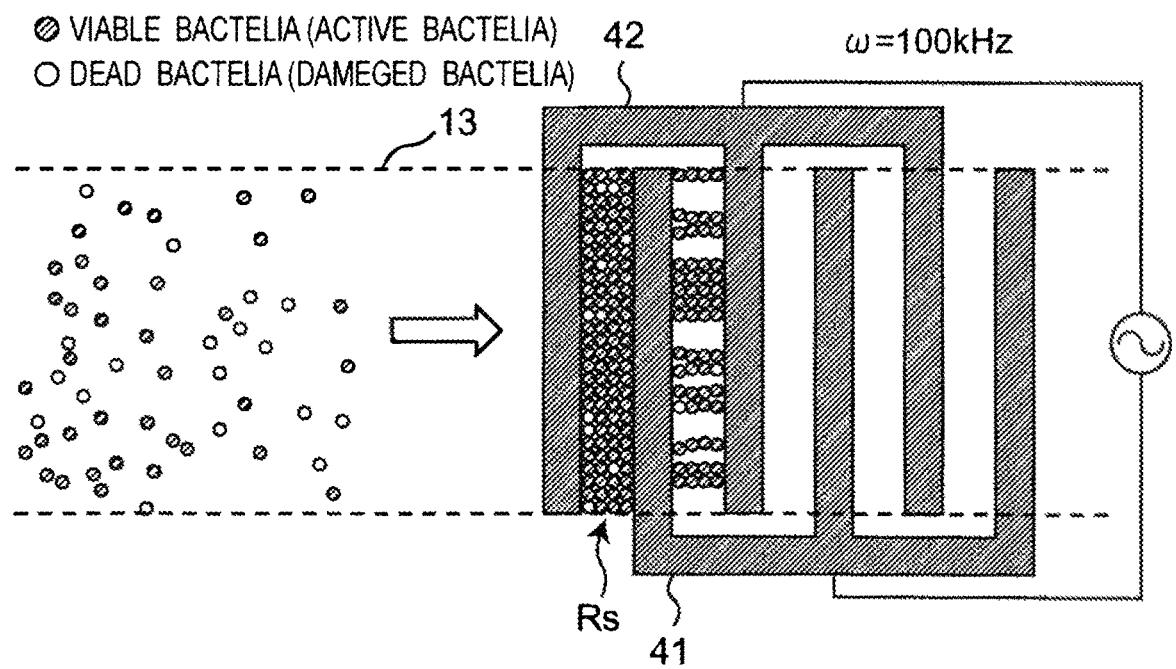
FIGS. 5A and 5B are diagrams for explaining the principle of the present inspection method.
Figure 5B:
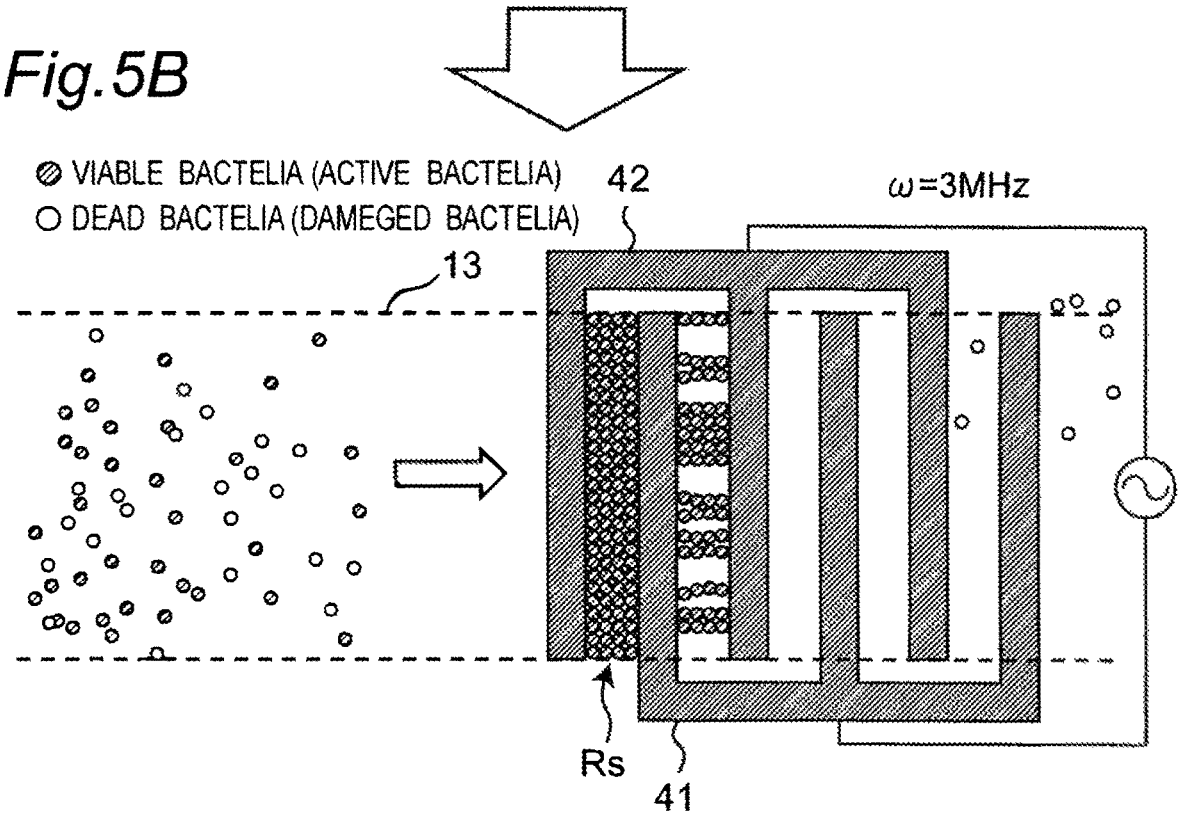

FIGS. 5A and 5B are explanatory diagrams of the principle of the inspection method according to the present embodiment.

In the inspection system and the inspection method according to the present embodiment, bacteria and the like of the inspection objects contained in the sample liquid are collected by using dielectrophoresis. As shown in FIG. 5A, when an AC voltage with a frequency $\omega$ is supplied between the electrodes 41 and 42, the dielectrophoresis force $F_{DEP}$ acting on bacteria such as viable bacteria and dead bacteria in the sample liquid flowing through the flow channel 13 is expressed by the following equation.

$$F_{DEP} = 2\pi r^3 \epsilon_m \mathrm{Re}[K(\omega)] \mathrm{gradient} E^2 \qquad (1)$$

In the above equation (1), r is the radius of dielectric particles such as viable bacteria and dead bacteria of the inspection objects, $\epsilon_m$ is the dielectric constant of the medium of the sample liquid, and E is the intensity of the electric field. Re[X] represents the real part of the complex number X. $K(\omega)$ is the Clausius-Mossotti factor and is expressed by the following equation.

$$K(\omega) = (\epsilon_p^* - \epsilon_m^*) / (\epsilon_p^* + 2\epsilon_m^*) \qquad (2)$$

In the above equation (2), $\epsilon_p^*$ ($=\epsilon_p + \rho_p/(j\omega)$) is the complex dielectric constant of the dielectric particles ($\epsilon_p$ is the dielectric constant of the dielectric particles and $\rho_p$ is the conductivity thereof). In addition, $\epsilon_m^*$ ($=\epsilon_m + \rho_m/(j\omega)$) is the complex dielectric constant of the medium ($\rho_m$ is the conductivity of the medium).

When $\mathrm{Re}[K(\omega)] > 0$ in the above equation (1), a positive dielectrophoresis force $F_{DEP}$ with respect to the installation direction of the electrodes 41 and 42 acts on the dielectric particles, and the dielectric particles are attracted to the vicinities of the electrodes 41 and 42 to be absorbed to the slit Rs. On the other hand, when $\mathrm{Re}[K(\omega)] < 0$, a negative dielectrophoresis force $F_{DEP}$ acts on the dielectric particles, and the dielectric particles repel the electrodes 41 and 42. Therefore, appropriately setting the frequency $\omega$ allows inspection objects to be selectively adsorbed to the slit Rs while removing impurities and the like other than the inspection objects.

Bacteria in the sample liquid are collected in the slit Rs by the action of positive dielectrophoresis force $F_{DEP}$. Since a bacterium has a predetermined size, the slit Rs is filled with bacteria to be saturated when a certain amount of bacteria are collected in the slit Rs. In the present system, saturation is reached in order from the upstream slit Rs in the flow channel 13, since the microelectrode unit 30 is set in such a manner that a plurality of slits Rs are arranged at predetermined intervals in the liquid flow direction in the flow channel 13.

Thus, in the present inspection method, the amount of bacteria and the like contained in the sample liquid is measured as follows by the user of the present system.

First, the amount of bacteria and the like per slit Rs to be collected when saturation occurs (saturation amount) is obtained in advance.

Next, the dielectrophoresis device 1 is controlled with the control device 20, whereby an AC voltage with a predetermined frequency is supplied from the AC voltage supply unit 11 to the microelectrode unit 30 in the flow channel 13 while a sample liquid flows from the pump unit 10 to the flow channel 13 of the collection unit 3, and a positive dielectrophoresis force is acted on the inspection objects.

Next, the region Rc in which the slits Rs in the microelectrode unit 30 are aligned (see FIG. 3) is captured, and the number of saturated slits Rs are counted in the captured image. The number of slits may be counted by image analysis performed on the captured image by the information processing device 21 or by the user based on the captured image displayed on the information processing device 21. Instead of imaging the region Rc, the user may directly look through the optical microscope to count the saturated slits Rs.

The amount of bacteria and the like of the inspection objects contained in the sample liquid is obtained by the product of the previously obtained saturation amount and the number of slits of the counting result. Therefore, by measuring the number of slits saturated with bacteria and the like trapped, the inspection objects contained in the sample liquid can be easily quantitatively evaluated.

The saturation amount of slit Rs can be calculated based on the type and size of bacteria and the like of the inspection objects. Depending on the inspection objects, the frequency w of the AC voltage is set in such a manner that a positive dielectrophoresis force acts, and the voltage amplitude of the AC voltage and the velocity of flow in the flow channel 13 are also controlled appropriately. Thus, various inspection objects can be selectively collected and quantitatively evaluated easily (details will be described below).

For example, frequency control can switch whether or not to distinguish between viable bacteria (active bacteria) and dead bacteria (damaged bacteria) in bacteria. FIG. 5A shows an example of collecting viable bacteria and dead bacteria together. For example, an AC voltage to the electrodes 41 and 42 at the frequency $\omega = 100$ kHz is supplied to cause a positive dielectrophoresis force to act on both viable bacteria and dead bacteria. According to this, both viable bacteria and dead bacteria can be collected distinguished from others and can be quantitatively evaluated.

FIG. 5B shows an example of selectively collecting viable bacteria. In the example shown in FIG. 5B, after the operation at the frequency $\omega = 100$ kHz as shown in FIG. 5A, the frequency $\omega$ is raised to 3 MHz. Then, while a positive dielectrophoresis force acts on viable bacteria, the positive dielectrophoresis force does not act on dead bacteria. Thus, only the viable bacteria can be adsorbed to the slit Rs, and the amount of viable bacteria other than dead bacteria can be easily quantitatively evaluated.

2-2. Evaluation Method

In the present system, various observation methods are available to count the slits saturated with bacteria and the like in the microelectrode unit 30, and to quantitatively evaluate bacteria and the like. In the following, evaluation method a of the amount of bacteria in the present system will be described with reference to FIGS. 6A to 6E.

Figure 6A:
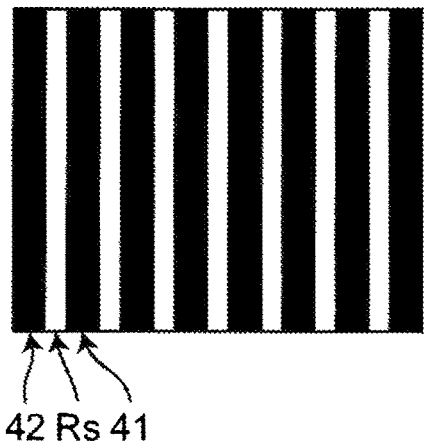
FIGS. 6A to 6E are diagrams for explaining an imaging method in the present system.
Figure 6B:
Figure 6C:
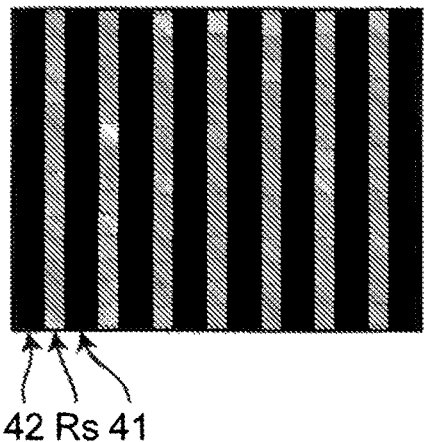
Figure 6D:
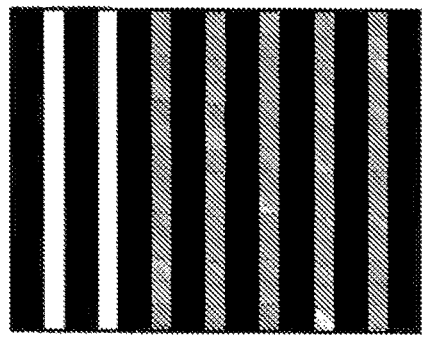
Figure 6E:
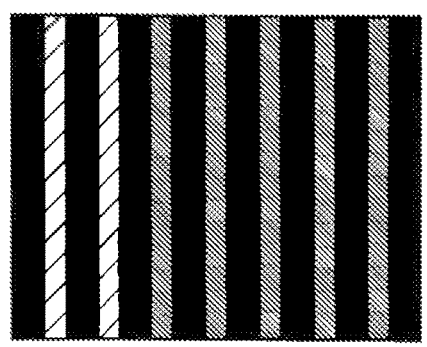

FIGS. 6A and 6B show imaging examples of states before and after the performance of dielectrophoresis in the phase contrast observation method. FIGS. 6C and 6D show imaging examples of states before and after the performance of dielectrophoresis in the bright field observation method. FIG. 6E shows an imaging example of a state after the performance of dielectrophoresis in the fluorescence observation method.

In the present embodiment, when phase contrast observation is performed, the phase contrast microscope is used in the imaging unit 12 (see FIG. 1). Then, in the initial state before the performance of dielectrophoresis, the region Rc of the microelectrode unit 30 is observed (imaged) as shown in FIG. 6A. That is, the electrodes 41 and 42 appear dark while the slit Rs appears bright. This is because the electrodes 41 and 42 are opaque while the slit Rs is transparent.

On the other hand, when dielectrophoresis is performed so that bacteria are collected in the slit Rs, the saturated slit Rs becomes dark as shown in FIG. 6B. This is because the slit Rs becomes opaque due to the accumulation of bacteria in the saturated slit Rs. Therefore, by counting the number of slits that remain bright as before and after the dielectrophoresis or counting the number of darkened slits, the amount of bacteria can be quantitatively evaluated.

When bright field observation is performed, an epi illumination microscope is used in the imaging unit 12. Then, in the initial state before the performance of dielectrophoresis, the region Rc of the microelectrode unit 30 is observed as shown in FIG. 6C. That is, both the electrodes 41 and 42 and the slit Rs appear dark with the adjustment of the reflected light of the light emitted from the epi illumination microscope.

On the other hand, when dielectrophoresis is performed so that bacteria are collected in the slit Rs, the saturated slit Rs appears bright with the reflected light from the collected bacteria as shown in FIG. 6D. In this case, by counting the number of slits appearing bright after the dielectrophoresis, the amount of bacteria can be quantitatively evaluated.

When fluorescence observation is performed, fluorescent labels are used for inspection objects in the sample liquid. Further, in the imaging unit 12, the epi illumination microscope in which, for example, a fluorescence filter or the like is appropriately set (fluorescence microscope) is used. The initial state before the dielectrophoresis in this case is the same as in the case of bright field observation (FIG. 6C). On the other hand, when dielectrophoresis is performed in the dielectrophoresis device 1 so that bacteria are collected in the slit Rs, the saturated slit Rs emits fluorescence as shown in FIG. 6E. Therefore, the slit Rs saturated after the dielectrophoresis appears more clearly, and it is easier to count the number of slits.

2-3. Experimental Results

Figure 7:
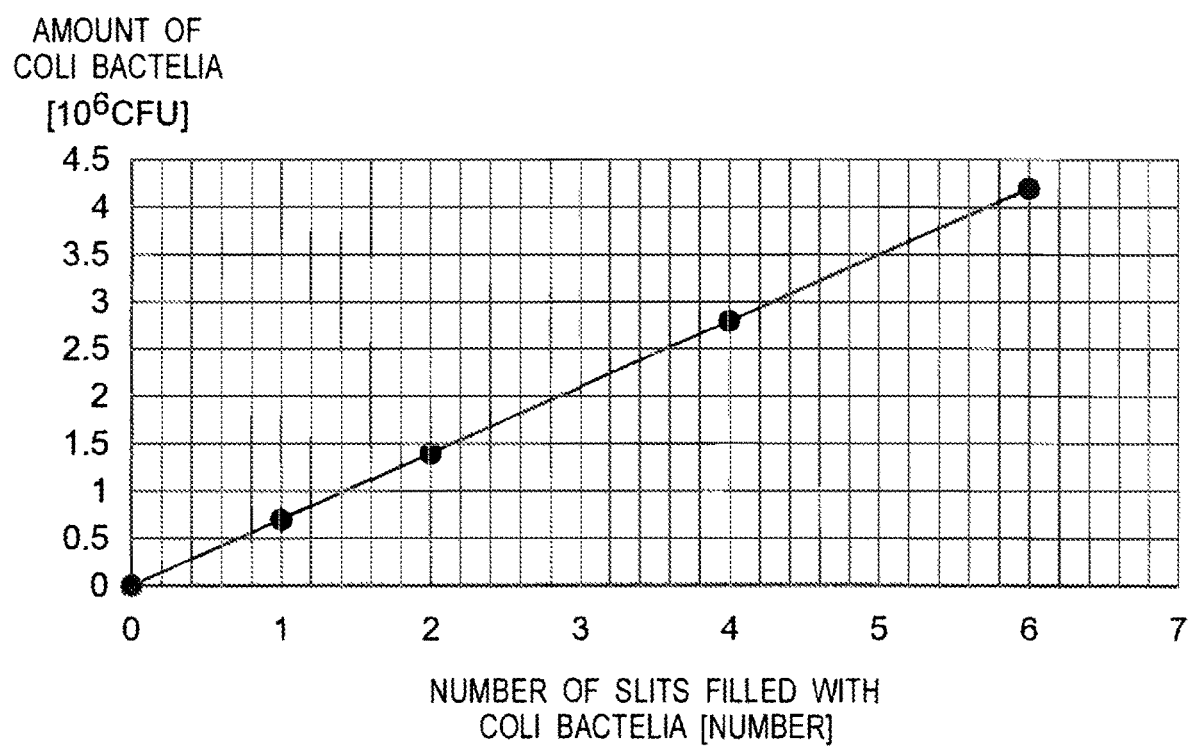
FIG. 7 is a graph showing a first experimental result of the inspection method according to the first embodiment.

In the following, experimental results of the inspection method according to the present embodiment will be described with reference to FIGS. 7 to 9F. FIG. 7 is a graph showing a first experimental result of the present inspection method. FIGS. 8A to 8E are captured images in the first experiment of the present inspection method.

In the first experiment shown in FIGS. 7 and 8A to 8E, coli bacteria (ATCC 11775) are used as experimental bacteria of the inspection objects. The above inspection method is performed a plurality of times by changing the amount of experimental bacteria in the sample liquid. As the imaging method, a phase contrast observation method is adopted (see FIGS. 6A and 6B).

In FIG. 7, the horizontal axis represents the number of slits in which the experimental bacteria are collected and filled until the experimental bacteria are saturated. The vertical axis represents the amount of experimental bacteria, and the unit of the vertical axis is $10^6$ CFU (colony forming unit).

Figure 8A:
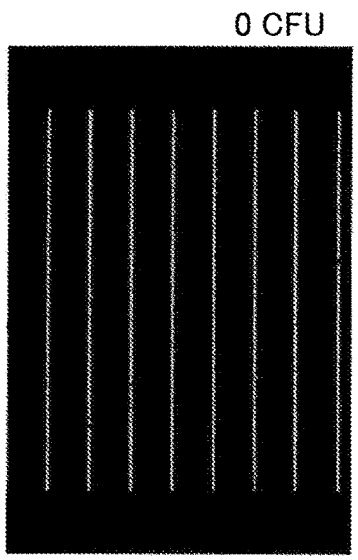
FIGS. 8A to 8E are captured images in the first experiment of the present inspection method.

FIGS. 8A to 8E show captured images corresponding to the respective experimental results plotted in the graph in FIG. 7. FIG. 8A shows a captured image in the initial state (0 CFU). FIGS. 8B to 8E show the captured images when the experimental bacteria amount is set to $0.7 \times 10^6$ CFU, $1.4 \times 10^6$ CFU, $2.8 \times 10^6$ CFU, and $4.2 \times 10^6$ CFU, respectively.

Figure 8B:
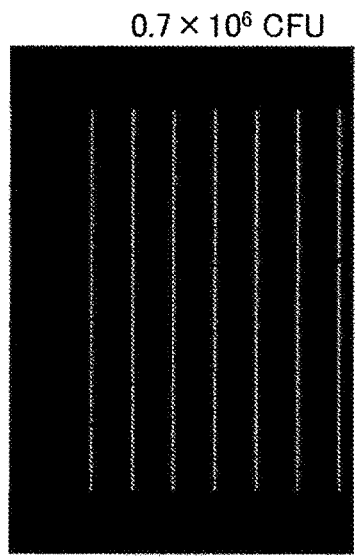
Figure 8C:
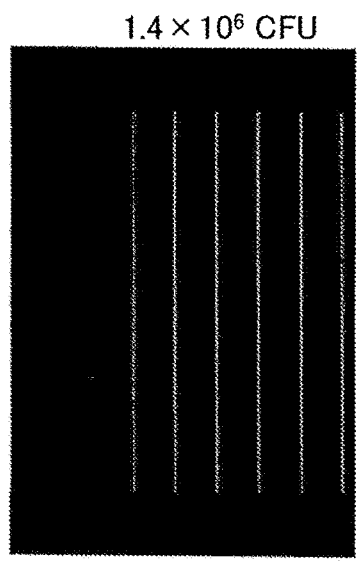

In FIG. 8A, all the eight slits appear bright corresponding to the fact that experimental bacteria are not collected in the initial state. In FIG. 8B, one slit, which appears bright at the left end in FIG. 8A, is dark. In FIG. 8C, one more slit is dark from the state in FIG. 8B. The darkened slit is a slit saturated (filled) with experimental bacteria contained in the sample liquid. In FIG. 8C, since the experimental bacteria amount approximately twice as large as that in FIG. 8B ($1.4 \times 10^6$ CFU) is set, it is understood that the number of darkened slits actually corresponds to the experimental bacteria amount contained in the sample liquid.

Figure 8D:
Figure 8E:

Also in FIGS. 8D and 8E, the number of darkened slits increases according to the increase of the experimental bacteria amount to $2.8 \times 10^6$ CFU and $4.2 \times 10^6$ CFU in order. As shown in FIG. 7, the number of darkened slits in FIGS. 8A to 8E is proportional to the experimental bacteria amount in each case. As described above, it is confirmed that counting the number of darkened slits allows the bacteria contained in the sample liquid to be easily and quantitatively evaluated.

FIGS. 9A to 9F are captured images in the second experiment of the present inspection method. In the second experiment, *S. Cerevisiae* is used as the experimental bacterium and epi illumination observation method is adopted as the imaging method (see FIGS. 6C and 6D).

Figure 9A:
FIGS. 9A to 9F are captured images in the second experiment of the present inspection method.
Figure 9B:
Figure 9C:
Figure 9D:
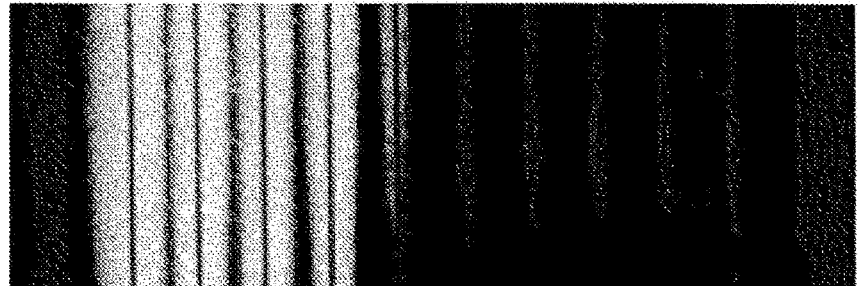
Figure 9E:
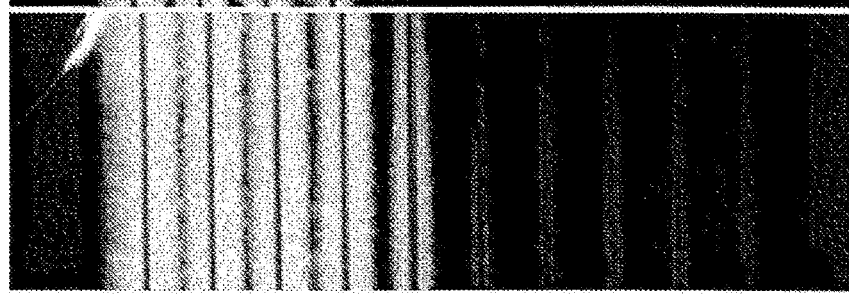
Figure 9F:
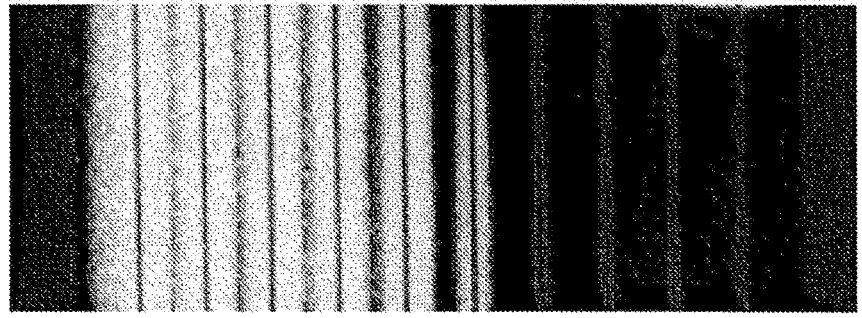

In FIGS. 9A to 9F, the saturated slit appears brighter based on the epi illumination observation method. In FIGS. 9A to 9F, the experimental bacteria amount is increased sequentially. In FIG. 9A, 0.5 slit appears bright. Subsequently, 1.0 slit in FIG. 9B, 2.0 slits in FIG. 9C, 3.5 slits in FIG. 9D, 4.0 slits in FIG. 9E, and 5.5 slits in FIG. 9F appear bright. From the view of FIGS. 9A to 9F, based on the epi illumination observation method in the second experiment, it is confirmed that counting the number of brightened slits allows the bacteria contained in the sample liquid to be easily and quantitatively evaluated.

3. Summary

As described above, the dielectrophoresis device 1 according to the present embodiment is an inspection device for inspecting an amount of the dielectric particles contained in the sample liquid. The dielectrophoresis device 1 includes the dielectric collection unit 3, the pump unit 10, and the AC voltage supply unit 11. The dielectric collection unit 3 includes at least the pair of electrodes 41 and 42 and the flow channel 13 extending in the predetermined liquid flow direction on the pair of electrodes 41 and 42. The pump unit 10 feeds the sample liquid to follow the flow channel 13 in the liquid flow direction. The AC voltage supply unit 11 supplies, to the pair of electrodes 41 and 42, the AC voltage with the predetermined frequency to cause dielectrophoresis for dielectric particles in the sample liquid. The dielectric collection unit 3 includes the plurality of slit regions Rs aligned in the liquid flow direction between the pair of electrodes 41 and 42. Each of the plurality of slit regions Rs is separated from each other within the flow channel 13.

Accordingly, in the plurality of slit regions Rs separated from each other aligned in the liquid flow direction in the flow channel 13, slits are saturated in order from the upstream side and can be counted in the order. Thus, the amount of bacteria, cells, and the like contained in the sample liquid can be easily inspected.

The inspection method according to the present embodiment is an inspection method for inspecting the amount of dielectric particles contained in the sample liquid. The present method includes: feeding the sample liquid in such a manner as to advance in a predetermined direction in the collection unit 3 including at least the pair of electrodes CH1 and CH2 arranged alternately at equal intervals of the plurality of slits Rs in the predetermined direction; supplying the AC voltage with the predetermined frequency to the pair of electrodes to cause dielectrophoresis for the dielectric particles in the fed sample liquid; and counting the slits saturated with the dielectric particles in the collection unit 3.

The inspection system according to the present embodiment includes the collection unit 3, the pump unit 10, the AC voltage supply unit 11, the imaging unit 12, and the information processing device 21. The collection unit 3 includes at least the pair of electrodes CH1 and CH2 arranged alternately at equal intervals of the plurality of slits Rs in the predetermined direction. The pump unit 10 feeds the sample liquid in such a manner that the sample liquid advances in the predetermined direction in the collection unit 3. The AC voltage supply unit 11 supplies the AC voltage with the predetermined frequency to the pair of electrodes CH1 and CH2 to cause dielectrophoresis for the dielectric particles in the fed sample liquid. The imaging unit 12 captures an image of a predetermined region Rc in which the plurality of slits Rs are aligned in the collection unit 3. The information processing device 21 analyzes the imaging result to count the slits Rs saturated with the dielectric particles.

Accordingly, counting the slits saturated with dielectric particles such as bacteria and cells allows the amount of bacteria, cells, and the like contained in the sample liquid to be easily inspected.

Second Embodiment

In the present inspection system, the supply voltage control over the electrode pairs CH1 and CH2 in the microelectrode unit 30 may be switched in stages. Multistage switching methods are available to perform quantitative evaluation with high accuracy filling each slit Rs with bacteria and the like as follows. A method of once holding the bacteria and the like of the inspection objects in the electrode pair CH1 on the upstream side and imaging the held bacteria and the like in the electrode pair CH2 on the downstream side will be described.

Figure 10A:
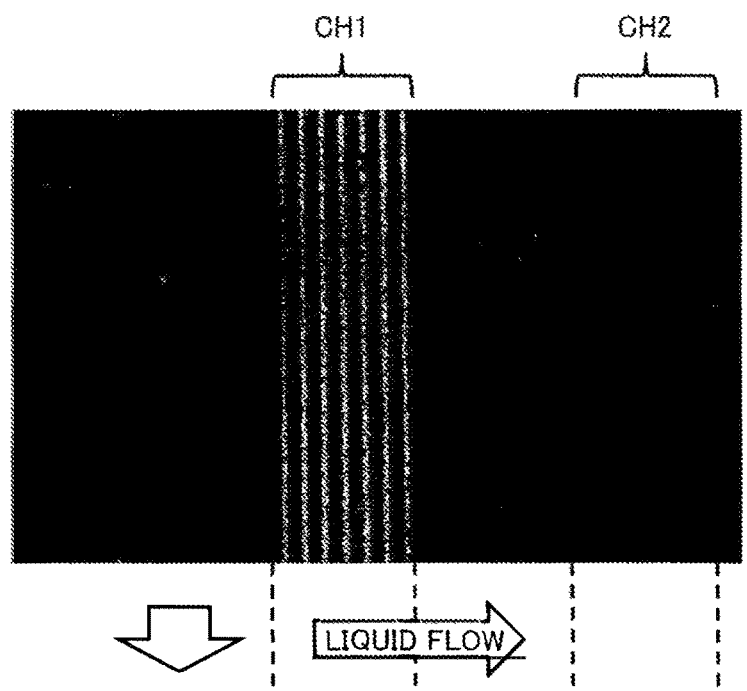
FIGS. 10A to 10C are images showing the states of the microelectrode unit in the multistage switching method according to a second embodiment.
Figure 10B:
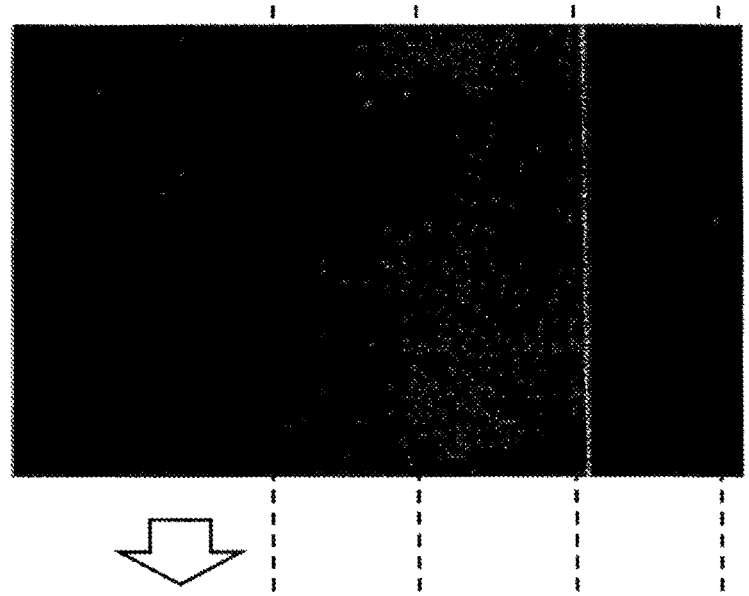
Figure 10C:
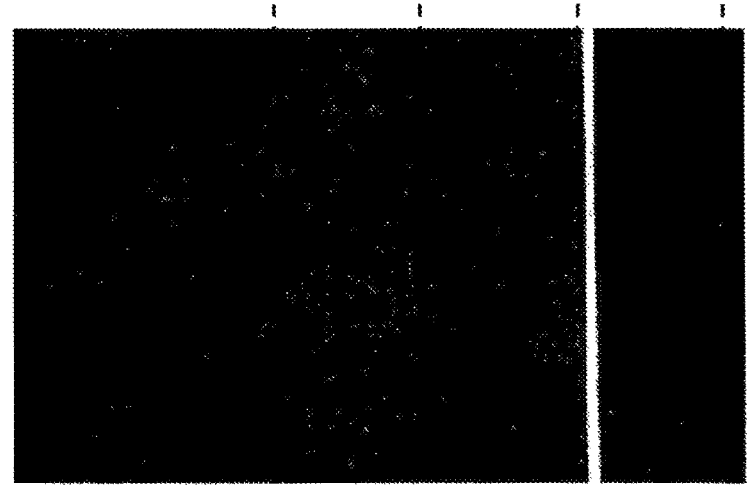
Figure 11:
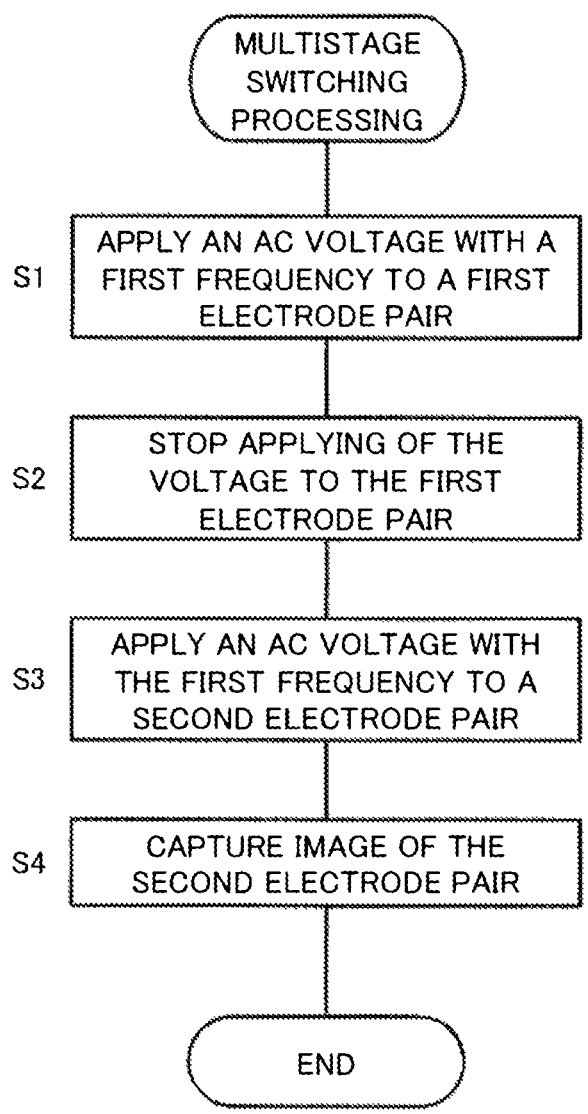
FIG. 11 is a flowchart showing multistage switching processing in the present system.
Figure 12A:
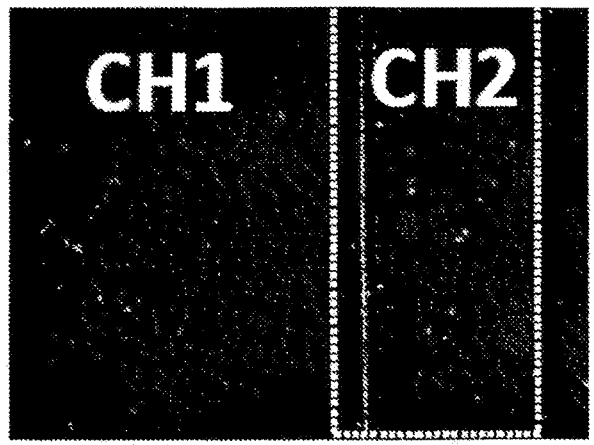
FIGS. 12A to 12D are diagrams for explaining the imaging processing in step S4 in FIG. 11.
Figure 12B:
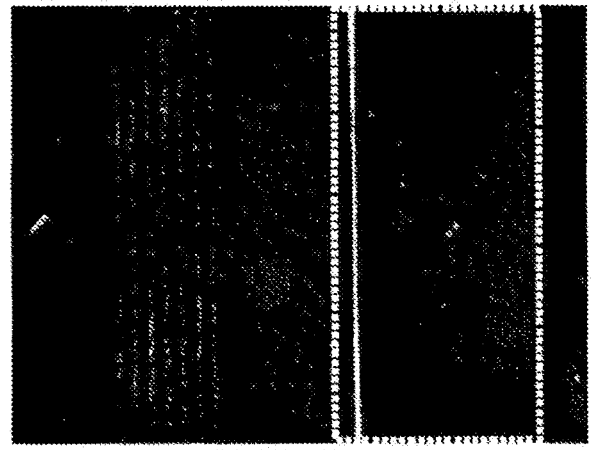
Figure 12C:
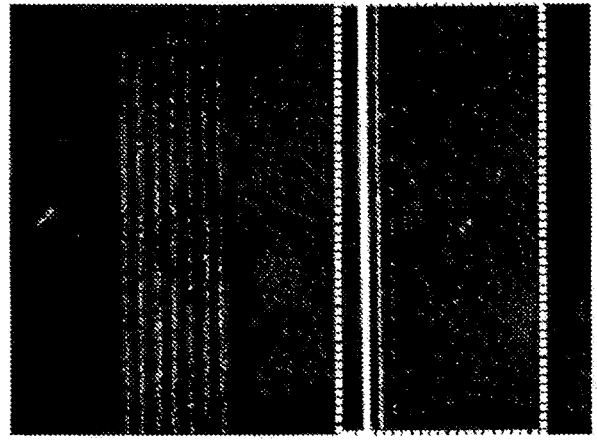
Figure 12D:
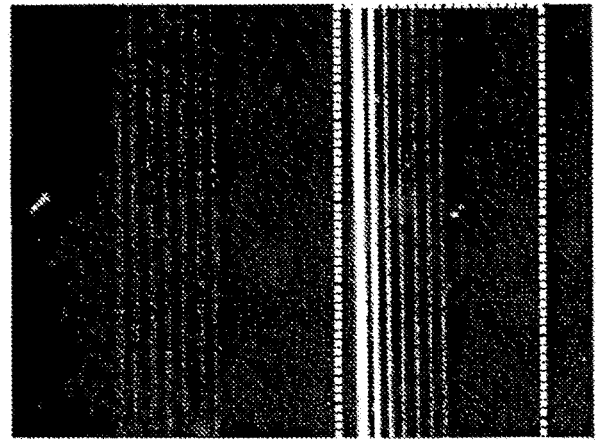

FIGS. 10A to 10C are images showing the states of the electrode pairs CH1 and CH2 of the microelectrode unit in the multistage switching method according to the second embodiment. FIG. 11 is a flowchart showing multistage switching processing according to the present embodiment.

First, the control device 20 controls the AC voltage supply unit 11 to supply an AC voltage with a first frequency to the first electrode pair CH1 for a predetermined period (for example, 1 to 10 minutes) (S1). The first frequency is a frequency for causing a positive dielectrophoresis force to act on the bacteria and the like of the objects of collection, and is set to, for example, 100 kHz (to collect viable bacteria and dead bacteria). The predetermined period can be set appropriately according to the inspection objects.

FIG. 10A shows an image of the first and second electrode pairs CH1 and CH2 after the processing in step S1 is performed. The image shown in FIG. 10A is an image based on the fluorescence observation (see FIG. 6E) (the same applies to FIGS. 10B and 10C). Performing the processing in step S1 for a predetermined period causes bacteria to be collected in a plurality of slits and held in the first electrode pair CH1 in FIG. 10A.

Next, the control device 20 stops supplying the AC voltage with the first frequency from the AC voltage supply unit 11 to the first electrode pair CH1 (S2). Then, no dielectrophoresis force acts on the bacteria in the first electrode pair CH1, and thus the held bacteria is released from the first electrode pair CH1 (see FIG. 10B).

Next, the control device 20 supplies the AC voltage with the first frequency from the AC voltage supply unit 11 to the second electrode pair CH2 (S3). In step S3, the control device 20 also controls the pump unit 10 to flow the sample liquid in the liquid flow direction with the amount of flow and the velocity of flow set appropriately.

FIG. 10B shows an image of the first and second electrode pairs CH1 and CH2 at the start of the processing in step S3. In FIG. 10B, the bacteria held in the first electrode pair CH1 moves in the liquid flow direction, and some of the bacteria reach the second electrode pair CH2.

FIG. 10C shows an image of the first and second electrode pairs CH1 and CH2 after a lapse of a predetermined period from the state shown in FIG. 10B. The processing in step S3 is performed for a predetermined period from the state shown in FIG. 10B, whereby bacteria are intensively collected in the upstream slit in the second electrode pair CH2 in FIG. 10C. It is considered that once holding the bacteria in the first electrode pair CH1 in step S1 causes the bacteria to move along the vicinity of the bottom of the flow channel in steps S2 and S3 and the dielectrophoresis force to act efficiently when the bacteria reach the second electrode pair CH2 positioned at the bottom of the flow channel.

Next, the control device 20 captures an image from the imaging unit 12 a specific region in which slits are aligned in the second electrode pair CH2 (S4). The region to be imaged is, for example, a region including the most upstream slit in the second electrode pair CH2 (see FIG. 12). The control of the imaging unit 12 in step S4 may be performed from the information processing device 21.

According to the above processing, the bacteria are once held in the first electrode pair CH1 on the upstream side in step S1, and the held bacteria are moved to the downstream side, and then collected again in the second electrode pair CH2. Therefore, the probability that bacteria are collected in order from the upstream slit can be improved in the second electrode pair CH2, and the accuracy of quantitative evaluation by counting the number of slits filled with bacteria can be improved.

FIGS. 12A to 12D are diagrams for explaining the imaging processing in step S4 in FIG. 11. In FIGS. 12A to 12D, the slits in the second electrode pair CH2 are filled with bacteria in order from the upstream side. Therefore, imaging the region enclosed by the broken line in the figure allows quantitative evaluation to be easily performed by counting the number of slits.

Figure 13:
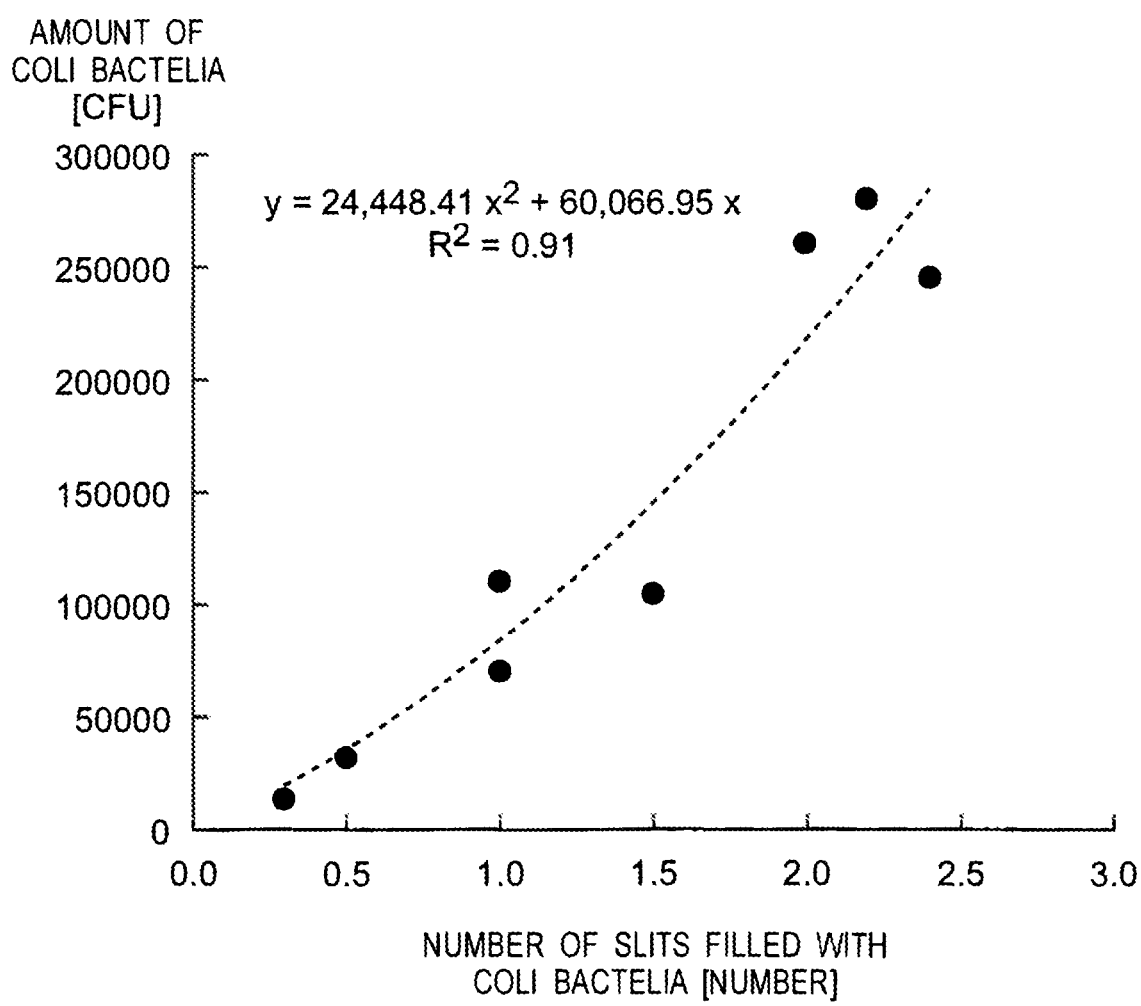
FIG. 13 is a graph showing an experimental result of the multistage switching method.

FIG. 13 is a graph showing an experimental result of the multistage switching method. In FIG. 13, the horizontal axis represents the number of slits filled with experimental bacteria in the second electrode pair CH2. The vertical axis represents the amount of experimental bacteria, and the unit of the vertical axis is CFU.

In the experiment shown in FIG. 13, coli bacteria (ATCC 11775) are used as experimental bacteria. The inspection method by multistage switching method is performed a plurality of times by changing the amount of experimental bacteria in the sample liquid. The first frequency of the AC voltage is set to 100 kHz and the voltage amplitude is set to 5 volts. The amount of experimental bacteria on the vertical axis is calculated from the viable bacteria evaluation method by the WST-1 method using a microplate reader. According to FIG. 13, it is confirmed that bacteria contained in the sample liquid can be easily evaluated quantitatively by counting the number of slits sequentially filled in order from the upstream in the downstream electrode pair CH2 in the multistage switching method.

In the above processing, the AC voltage with one kind of frequency (first frequency) is supplied in the electrode pairs CH1 and CH2, but the frequency of the AC voltage supplied to the electrode pairs CH1 and CH2 may be switched. In the following, an example of a method for separating viable bacteria from dead bacteria by switching the frequency of the AC voltage will be described with reference to FIG. 14.

Figure 14:
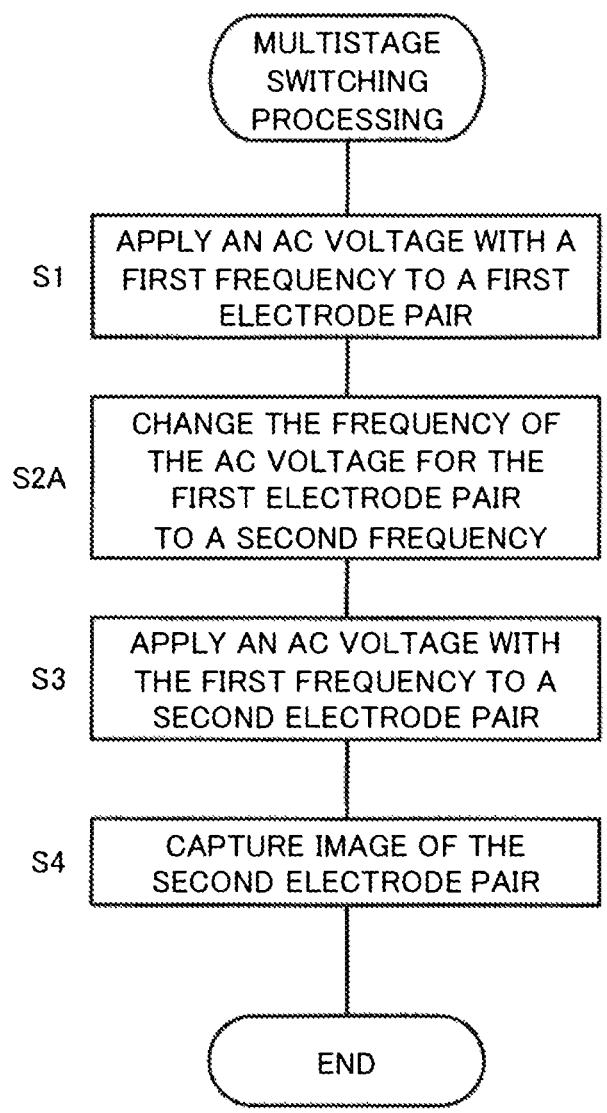
FIG. 14 is a flowchart showing a modified example of the multistage switching processing.

FIG. 14 is a flowchart showing a modified example of the multistage switching processing in FIG. 13. In the processing shown in FIG. 14, instead of stopping the supply of the AC voltage to the first electrode pair CH1 in step S2 in FIG. 13, the frequency of the AC voltage is switched from the first frequency to the second frequency (S2A). The second frequency is a frequency for causing a positive dielectrophoresis force to act on the bacteria and the like as the objects to be held in the first electrode pair CH1, and is set to, for example, 3 MHz (only viable bacteria are held). Then, out of the bacteria held in step S1 in the first electrode pair CH1, the dielectrophoresis force does not act only on dead bacteria, and the dead bacteria are released from the first electrode pair CH1.

Next, in step S3, the AC voltage with the first frequency capable of collecting dead bacteria is supplied to the second electrode pair CH2. Therefore, only the dead bacteria are collected in the second electrode pair CH2 in order from the upstream slit, and the viable bacteria remain held in the first electrode pair CH1. Therefore, in the following step S4, capturing of the specific region of the second electrode pair CH2 allows a captured image in a state filled with dead bacteria in order from the upstream slit to be obtained.

With the above processing, among the viable bacteria and dead bacteria held in the first electrode pair CH1, only dead bacteria are selectively re-collected in the second electrode pair CH2. Accordingly, quantitative evaluation can be easily performed with the distinction between viable bacteria and dead bacteria.

In addition, in the above processing, when viable bacteria are used as inspection objects, in step S4, the region of measurement in the first electrode pair CH1 may be imaged. In addition, when both viable bacteria and dead bacteria are compared, in step S4, a region including the first and second electrode pairs CH1 and CH2 may be imaged.

Other Embodiments

In the above embodiments, bacteria and cells are exemplified as inspection objects of the present system. The inspection objects of the present system are not limited to bacteria and cells, and may be various dielectric particles, and may be, for example, microorganisms, fungi, spores, and viruses.

In the above embodiments, the collection unit 3 in which two electrode pairs CH1 and CH2 are provided for one flow channel 13 is described. The flow channel and the electrode pair in the collection unit are not limited to this, and, for example, a plurality of flow channels or branched flow channels may be provided, or one or more electrode pairs may be provided for each flow channel.

Although the processing of each step in the flowcharts in FIGS. 11 and 14 is performed by the control device 20 in the above embodiments, the processing may be performed by the user of the present system or may be performed by the user's operation of the control device 20.

In the above embodiments, the first frequency of the AC voltage supplied in step S1 in FIG. 11 exemplifies 1 kHz. When only the viable bacteria are to be inspection objects, for example, the first frequency of the AC voltage supplied in step S1 may be set to a value at which the dielectrophoresis force acts only on viable bacteria, such as 3 MHz. Thus, in step S4 in FIG. 11, a captured image of the slits filled in order only with viable bacteria in the second electrode pair CH2 is obtained.

In the above embodiments, the illustrated example is that each protruding part and each slit of the electrodes 41 and 42 of the collection unit 3 (dielectric collection unit) extend in a direction orthogonal to the liquid flow direction. The slits in the dielectric collection unit need not be orthogonal to the liquid flow direction (the longitudinal direction of the flow channel 13), and may cross at a predetermined angle (for example, 45 degrees or more) with respect to the liquid flow direction.

In the above embodiments, the illustrated example is that the slit between each protruding part of the electrodes 41 and 42 is linearly formed with the predetermined width W2. The shape of the slit may be, for example, curved or bent, or the width W2 for each slit may be different. Further, the plurality of slits may not be parallel to each other, and for example, the slits may be arranged side by side within a range of a predetermined angle.

In the above embodiments, the dielectrophoresis device 1 (inspection device) including an imaging unit 12 is described. The inspection device according to the present invention may not include the imaging unit 12. For example, he instead of (or in addition to) the imaging unit 12, the inspection device may include a microscope having an eyepiece or the like for the user to directly observe the region Rc.

In addition, the image analysis by the inspection system in the above embodiments may be performed by, for example, an area analysis method. Specifically, the image analysis unit (information processing device 21) calculates the area of the saturated slits Rs in the region Rc of the observation target, and divides the calculated area by a ratio of an effective area, which is a ratio of the region Rc to the entire region in which the slits Rs in the flow channel 13 are aligned. According to this method, the counting of saturated slits, that is, the measurement of the amount of bacteria can be performed with high accuracy.

In the above embodiments, although an example of the inspection system is described that the information processing device 21 constitutes the display unit and the image analysis unit, the display unit and the image analysis unit may be configured separately. Further, the display unit or the image analysis unit may be configured integrally with the inspection device (dielectrophoresis device 1). Further, when the slits are counted visually by the user, the image analysis unit may be omitted in the inspection system.

Summary of Aspects

As described above, 1st aspect according to the present invention is an inspection device (1) for inspecting an amount of dielectric particles contained in a sample liquid. The inspection device includes a dielectric collection unit (3), a pump unit (10) and an AC voltage supply unit (11). The dielectric collection unit includes at least one pair of electrodes (41, 42) and a flow channel (13) extending in a predetermined direction on the pair of electrodes. The pump unit is configured to feed the sample liquid to follow the flow channel in the predetermined direction. The AC voltage supply unit is configured to supply, to the pair of electrodes, an AC voltage with a predetermined frequency to cause dielectrophoresis for dielectric particles in the fed sample liquid. The dielectric collection unit includes a plurality of slit regions (Rs) aligned in the predetermined direction between the pair of electrodes. Each of the plurality of slit regions is separated from each other within the flow channel.

2nd aspect according to the present invention is the inspection device of the 1st aspect, wherein a region in which the plurality of slit regions are connected to each other between the pair of electrodes is arranged outside the flow channel.

3rd aspect according to the present invention is the inspection device of the 1st or 2nd aspect, wherein the at least one pair of electrodes includes a first electrode pair (CH1) and a second electrode pair (CH2) disposed on a downstream side of the first electrode pair in the flow channel. The plurality of slit regions are famed between the second electrode pairs. The AC voltage supply unit supplies the AC voltage to the first electrode pair and then supplies the AC voltage to the second electrode pair.

4th aspect according to the present invention is the inspection device of the 3rd aspect, wherein the AC voltage supply unit stops supply of the AC voltage to the first electrode pair, and while stopping supply of the AC voltage to the first electrode pair, the AC voltage supply unit supplies the AC voltage to the second electrode pair.

5th aspect according to the present invention is the inspection device of the 3rd aspect, wherein the AC voltage supply unit changes a frequency of an AC voltage supplied to the first electrode pair, and while supplying an AC voltage with a changed frequency to the first electrode pair, the AC voltage supply unit supplies the AC voltage to the second electrode pair.

6th aspect according to the present invention is the inspection device of any one of the 1st to 5th aspects, wherein the dielectric particles include at least one of bacteria, cells, microorganisms, fungi, spores, and viruses.

7th aspect according to the present invention is the inspection device of any one of the 1st to 6th aspects further including the imaging unit (12) configured to capture an image of a predetermined region in which the plurality of slit regions are aligned in the dielectric collection unit.

8th aspect according to the present invention is an inspection system including the inspection device according to the 7th aspect and a display unit (21) configured to display an image captured by the imaging unit of the inspection device.

9th aspect according to the present invention is the inspection device of the 8th aspect further including an image analysis unit (21) configured to analyze an image captured by the imaging unit to count slits saturated with the dielectric particles.

10th aspect according to the present invention is the inspection device of the 9th aspect, wherein the sample liquid contains a fluorescent label causing the dielectric particles to emit fluorescence. The image analysis unit counts the saturated slits based on fluorescence emission in the captured image.

11th aspect according to the present invention is the inspection device of the 9th or 10th aspect, wherein the image analysis unit applies an area analysis method to the captured image to count the saturated slits.

12th aspect according to the present invention is an inspection method for inspecting an amount of dielectric particles contained in a sample liquid. The method includes feeding the sample liquid to follow a flow channel in a predetermined direction in a dielectric collection unit. The dielectric collection unit includes at least one pair of electrodes (41, 42) and the flow channel (13) extending in the predetermined direction on the pair of electrodes. The method includes supplying, to the pair of electrodes, an AC voltage with a predetermined frequency to cause dielectrophoresis for dielectric particles in the fed sample liquid. The method includes counting slits saturated with the dielectric particles among a plurality of slits aligned in the predetermined direction between the pair of electrodes in the dielectric collection unit.

13th aspect according to the present invention is the inspection method of the 12th aspect, wherein the sample liquid contains a fluorescent label causing the dielectric particles to emit fluorescence. The counting is adapted to count slits that emit fluorescence as the saturated slits.

14th aspect according to the present invention is the inspection method of the 12th or 13th aspect, wherein the at least one pair of electrodes includes a first electrode pair and a second electrode pair disposed on a downstream side of the first electrode pair in the flow channel. The supplying includes supplying the AC voltage to the first electrode pair, stopping supply of the AC voltage to the first electrode pair and supplying the AC voltage to the second electrode pair. The counting is adapted to count the saturated slits in the second electrode pair.

15th aspect according to the present invention is the inspection method of the 12th or 13th aspect, wherein the at least one pair of electrodes includes a first electrode pair and a second electrode pair disposed on a downstream side of the first electrode pair in the flow channel. The supplying includes supplying the AC voltage to the first electrode pair, changing a frequency of an AC voltage supplied to the first electrode pair and supplying the AC voltage to the second electrode pair. The counting is adapted to count the saturated slits in the second electrode pair.

What is claimed:

1. An inspection device for inspecting an amount of dielectric particles contained in a sample liquid, the inspection device comprising:
    a dielectric collection chip including at least one pair of electrodes and a flow channel extending in a predetermined direction on the pair of electrodes;
    a pump configured to feed the sample liquid to follow the flow channel in the predetermined direction; and
    an AC voltage supply configured to supply, to the pair of electrodes, an AC voltage with a predetermined frequency to cause dielectrophoresis for dielectric particles in the fed sample liquid,
    wherein the dielectric collection chip includes a plurality of slit regions aligned in the predetermined direction between the pair of electrodes, and
    wherein each of the plurality of slit regions is separated from each other within the flow channel and defined by a boundary of the pair of electrodes to coincide with an interval between the pair of electrodes in the flow channel.

2. The inspection device according to claim 1, wherein a region in which the plurality of slit regions are connected to each other between the pair of electrodes is arranged outside the flow channel.

3. The inspection device according to claim 1,
    wherein the at least one pair of electrodes comprises a first electrode pair and a second electrode pair disposed on a downstream side of the first electrode pair in the flow channel,
    wherein the plurality of slit regions are formed between the second electrode pairs, and wherein the AC voltage supply supplies the AC voltage to the first electrode pair and then supplies the AC voltage to the second electrode pair.

4. The inspection device according to claim 3,
wherein the AC voltage supply stops supply of the AC voltage to the first electrode pair, and
while stopping supply of the AC voltage to the first electrode pair, the AC voltage supply supplies the AC voltage to the second electrode pair.

5. The inspection device according to claim 3,
wherein the AC voltage supply changes a frequency of an AC voltage supplied to the first electrode pair, and
while supplying an AC voltage with a changed frequency to the first electrode pair, the AC voltage supply supplies the AC voltage to the second electrode pair.

6. The inspection device according to claim 1, wherein the dielectric particles include at least one of bacteria, cells, microorganisms, fungi, spores, and viruses.

7. The inspection device according to claim 1, further comprising
an imager configured to capture an image of a predetermined region in which the plurality of slit regions are aligned in the dielectric collection chip.

* * * * *